(12) United States Patent
Åkerfeldt (10) Patent No.: US 8,308,758 B2
(45) Date of Patent: *Nov. 13, 2012

(54) CLOSURE DEVICE

(75) Inventor: Dan Åkerfeldt, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/997,858

(22) Filed: Nov. 29, 2004

(65) Prior Publication Data

US 2005/0080452 A1    Apr. 14, 2005

Related U.S. Application Data

(63) Continuation of application No. 10/166,725, filed on Jun. 12, 2002, now Pat. No. 6,939,363.

(51) Int. Cl.
*A61M 31/00* (2006.01)
*A61B 17/08* (2006.01)

(52) U.S. Cl. .......................... 606/213; 604/60

(58) Field of Classification Search ............... 606/214, 606/232, 108, 191, 198, 187, 213; 604/59, 604/60, 64, 195–197
See application file for complete search history.

(56) References Cited

U.S. PATENT DOCUMENTS

| | | | |
|---|---|---|---|
| 3,871,099 A | 3/1975 | Kahn | |
| 4,744,364 A | 5/1988 | Kensey | |
| 4,852,568 A | 8/1989 | Kensey | |
| 4,890,612 A | 1/1990 | Kensey | |
| 5,046,497 A * | 9/1991 | Millar | 600/309 |
| 5,061,274 A * | 10/1991 | Kensey | 606/213 |
| 5,108,421 A | 4/1992 | Fowler | |
| 5,357,978 A | 10/1994 | Turk | |
| 5,391,183 A | 2/1995 | Janzen et al. | |
| 5,437,631 A * | 8/1995 | Janzen | 604/506 |
| 5,643,318 A | 7/1997 | Tsukernik et al. | |
| 5,649,959 A | 7/1997 | Hannam et al. | |
| 5,725,498 A | 3/1998 | Janzen et al. | |
| 5,741,223 A | 4/1998 | Janzen et al. | |

(Continued)

FOREIGN PATENT DOCUMENTS

EP    1 371 333 B1    5/2004

(Continued)

OTHER PUBLICATIONS

Dan Akerfeldt, USPTO Notice of Allowance, U.S. Appl. No. 10/994,519, Aug. 31, 2011, 10 pages.

*Primary Examiner* — Katherine Dowe
(74) *Attorney, Agent, or Firm* — Foley & Lardner LLP (57) ABSTRACT

The invention provides a closure device (1) for sealing an incision channel leading through a vessel wall and into the vessel. The closure device (1) comprises a haemostatic material (3), which is contained in the distal end of an elongated insertion assembly (2). The insertion assembly (2), which comprises a stationary part (4) and a retractable part (5) being slidably movable with regard to each other, is adapted to be attached to an introducer (7) being in position in the incision channel, so that the insertion assembly (2) can be slid along the introducer (7) until the distal end of the insertion assembly (2) is in contact with the vessel wall, where the haemostatic material (3) is delivered in the incision channel by a retracting movement of the retractable part (5).

16 Claims, 4 Drawing Sheets

U.S. PATENT DOCUMENTS

| | | | |
|---|---|---|---|
| 5,830,130 A | 11/1998 | Janzen et al. | |
| 5,902,331 A | 5/1999 | Bonner et al. | |
| 5,948,425 A * | 9/1999 | Janzen et al. | 424/422 |
| 6,261,258 B1 * | 7/2001 | Saines | 604/58 |
| 6,277,094 B1 | 8/2001 | Schendel | |
| 6,325,789 B1 | 12/2001 | Janzen et al. | |
| 6,334,865 B1 * | 1/2002 | Redmond et al. | 606/213 |
| 6,368,341 B1 | 4/2002 | Abrahamson | |
| 6,371,975 B2 * | 4/2002 | Cruise et al. | 606/214 |
| 6,475,177 B1 * | 11/2002 | Suzuki | 604/11 |
| 6,610,069 B2 * | 8/2003 | Euteneuer et al. | 606/108 |
| 6,939,363 B2 * | 9/2005 | Åkerfeldt | 606/213 |
| 2002/0032432 A1 * | 3/2002 | Nash et al. | 604/533 |
| 2005/0131459 A1 * | 6/2005 | Akerfeldt | 606/214 |

FOREIGN PATENT DOCUMENTS

| | | |
|---|---|---|
| WO | WO 00/33744 | 6/2000 |
| WO | WO 00/33744 A1 | 6/2000 |

* cited by examiner

Fig. 15

CLOSURE DEVICE

The present application is a continuation of U.S. application Ser. No. 10/166,725, filed Jun. 12, 2002, issued as U.S. Pat. No. 6,939,363, the entire contents of which are incorporated herein by reference.

BACKGROUND OF THE INVENTION

The present invention relates generally to a closure device for sealing a percutaneous puncture in a vessel, in particular a closure device with which haemostatic material is introduced in the incision channel leading to the puncture hole in the vessel wall, thereby sealing the percutaneous puncture without obstructing the flow inside the vessel and without the risk that the haemostatic material unintentionally is introduced into the vessel.

During certain types of medical surgery or treatment, an introducer is used to access the vascular system of a patient. The introducer is inserted through the wall of a blood vessel in order to obtain access to the vascular system and may thereafter be used for guiding medical instruments such as catheters, guide wires and the like. After the completion of the medical procedure, there will be an incision or a wound in the wall of the blood vessel corresponding to the size of the introducer. The bleeding from the wound, which is the result of such a surgical operation, may be stopped by applying direct pressure on the wound. However, applying external pressure on the wound will require assistance of additional medical personnel and may also obstruct the flow of blood through the vessel.

U.S. Pat. No. 4,744,364 and U.S. Pat. No. 4,852,568, both of which are granted to Kensey Nash Corp., disclose how a closure means can be inserted into a blood vessel and then retracted in such a way that the engagement surface of the closure means haemostatically engages the inner surface of the blood vessel contiguous with the puncture, thereby stopping the bleeding from the puncture wound. In U.S. Pat. No. 4,890,612, which is also granted to Kensey Nash Corp., a sealing device comprises a plug means having a holding portion to be positioned in engagement with the inner surface of a vessel and a sealing portion formed of a foam material that extends into the punctured vessel to engage tissue contiguous therewith to seal the puncture wound.

As is recognized in U.S. Pat. No. 6,368,341, which is granted to Abrahamson, a drawback with the types of sealing devices described in the above-mentioned U.S. Pat. Nos. 4,744,364, 4,852,568 and 4,890,612 is that an intra-arterial sealing device extending into a blood vessel may obstruct the flow of blood therethrough. The sealing device according to U.S. Pat. No. 6,368,341 comprises a haemostatic closure device and a locating device having one or several locating members to be positioned against the inner surface of the vessel wall. The locating members are designed to provide a sufficient amount of resistance against retracting movement, so that a user is provided with an indication that the locating members are in contact with the inner vessel wall. When correctly positioned, the haemostatic closure device, which may include a clotting agent, is in the incision channel outside the vessel wall and there are no portions extending into the vessel, where such portions may obstruct the flow of blood.

SUMMARY OF THE INVENTION

However, a drawback with this sealing device is the potential risk that the locating members damage the inner vessel wall during the positioning operation, i.e. when a user retracts the locating device until he or she feels the resistance from the inner vessel wall. Such a risk is still present even if the locating members—as is stated in U.S. Pat. No. 6,368,341— are formed and shaped to minimize any potential damage to the blood vessel.

A more general problem encountered with closure devices of the type shown in U.S. Pat. No. 6,368,341 is the potential risk that a sealing member is deployed inside the blood vessel, instead of in the incision channel leading to the puncture hole in the vessel. This may for instance occur if a user misinterprets a resistance to retracting movement in the locating device as coming from the inner vessel wall, or accidentally pushes the whole haemostatic closure device too far into the incision channel before deploying the sealing member. The potential problem that a sealing member or a haemostatic material unintentionally is introduced into the vessel itself, instead of being positioned in the incision channel leading to the puncture hole in the vessel wall, can from a general point of view be ascribed to the fact that the closure devices known in the state of the art have access to the vessel through the puncture hole in the vessel wall.

This problem prevails also in U.S. Pat. No. 5,108,421, which is granted to Fowler and discloses how a vessel plug can be positioned against the outer surface of a vessel wall. During the positioning of the vessel plug, an inflated balloon is positioned against the inner surface of the vessel wall, thereby providing a support for the vessel plug and preventing the vessel plug from extending into the vessel. Nevertheless, the sealing member, here a vessel plug, has also in this case access to the vessel, and a user can by accident push the closure device too far into the incision channel and thereby deploy the sealing member inside the vessel.

In U.S. Pat. Nos. 5,391,183; 5,725,498; 5,741,223; 5,830,130; 5,948,425 and 6,325,789, all of which are granted to Janzen et al., devices are disclosed for inserting haemostatic material through a tissue channel and against the outside wall of a blood vessel, wherein the blood vessel wall has a puncture therein adjacent the tissue channel. Although the devices according to Janzen et al. have different designs, the same problem is encountered also here, i.e. that the haemostatic materials have access to the blood vessel through the puncture hole in the vessel wall.

Thus, there is a need in the art for a closure device that eliminates the risk that any sealing material unintentionally is introduced into a vessel. At the same time, the sealing material of such a closure device should not obstruct the fluid flow inside the vessel once the sealing operation has been completed.

The present invention discloses how a percutaneous incision leading to a vessel can be sealed without the risk that any sealing material unintentionally is introduced into the vessel itself. The closure device according to the present invention comprises basically an elongated insertion assembly and a charge of haemostatic material, which is contained in the distal portion of the insertion assembly. The insertion assembly, in turn, comprises a stationary part and a retractable part, which is in slidable engagement with the stationary part. The first step in a sealing operation is to connect the insertion assembly to the outside of an existing introducer, which already has been inserted into a vessel through an opening in the vessel wall in order to carry out the medical operation that made the percutaneous incision necessary. The insertion assembly is then slid along the introducer until it is in contact with the outer vessel wall. Thereafter, the charge of haemostatic material is delivered in the incision channel by retracting the retractable part of the insertion assembly. During this procedure, neither the insertion assembly nor the haemostatic material has access to the vessel itself, since the opening in the vessel wall is fully occupied by the inserted introducer. This eliminates the risk that the haemostatic material unintentionally is introduced into the vessel. Furthermore, the closure device has no parts that extend into the vessel, so the fluid flow inside the vessel remains unaffected after the completion of the sealing operation.

DETAILED DESCRIPTION OF THE PREFERRED EMBODIMENTS

Figure 1:
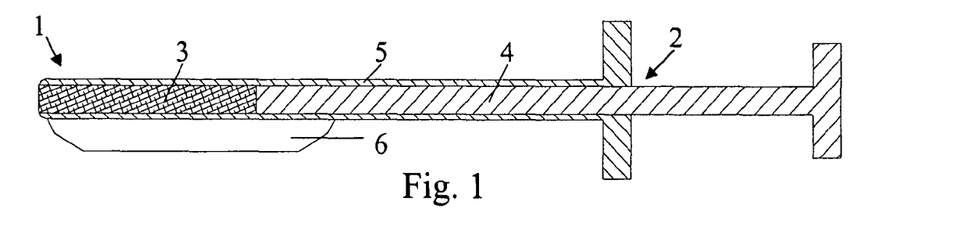
FIG. 1 shows schematically a first embodiment of a closure device according to the present invention.

In FIG. 1 is illustrated a first embodiment of a closure device 1 according to the present invention. The closure device 1 comprises an elongated insertion assembly 2 and a haemostatic or sealing material 3, which is contained in the distal portion of the insertion assembly 2. Preferably the haemostatic material 3 is impregnated or in some other way provided with a suitable clotting agent such as thrombin. The insertion assembly 2, in turn, comprises two parts, an elongated stationary part 4 and an elongated retractable part 5. Basically, the stationary part 4 has the shape of a rod, the distal end of which is in contact with the haemostatic material 3, and the retractable part 5 is in the form of a hollow sheath, which is in slidable engagement with the outside of the stationary part 4. Parts 4 and 5 may be made from any suitable material, such as plastic or metal. In FIG. 1, the closure device 1 is depicted in an initial state, with the distal portion of the retractable part 5 extending from the distal portion of the stationary part 4, thereby creating a space in which the haemostatic material 3 is accommodated. The proximal ends of the stationary part 4 and the retractable part 5 are advantageously provided with suitable handles, which extend perpendicular to the longitudinal axis of the insertion assembly 2 and which are adapted to facilitate the operation of the closure device 1. Such handles can have a variety of shapes and are not described in any detail. As mentioned above, a closure device according to the present invention is intended to be slidably attached to an existing introducer. This attachment can be accomplished by different attachment means, examples of which are described below. In this embodiment, the insertion assembly 2 comprises an attachment member 6, which is provided on the outside of the retractable part 5 and the function and form of which are described in more detail below.

Figures 2, 11, 12:
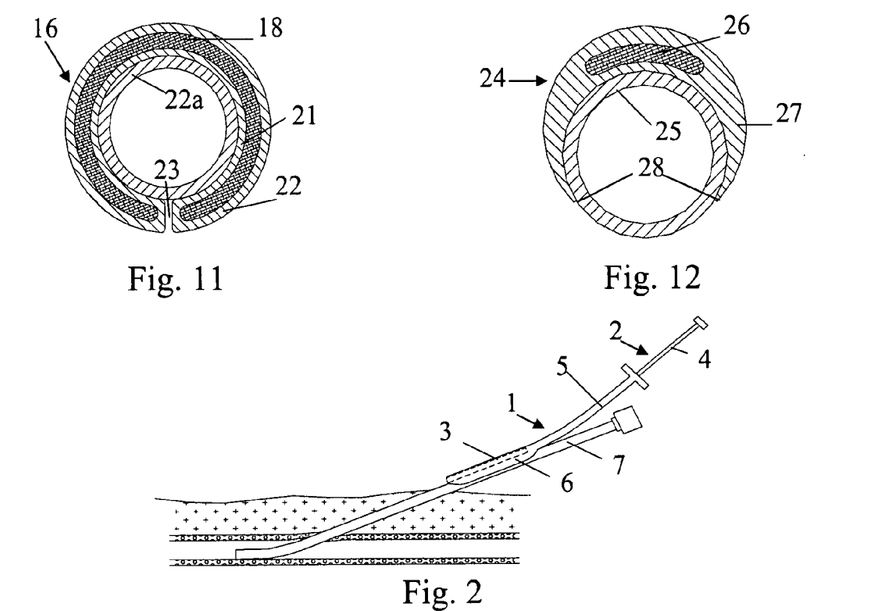
FIG. 2 illustrates schematically how the closure device of FIG. 1 is connected to an existing introducer in a first step of a sealing operation.
FIG. 11 shows the cross-section of the closure device of FIG. 10.
FIG. 12 shows the cross-section of a fourth embodiment of a closure device.

A closure device according to the present invention is designed for use in connection with an existing medical device such as an introducer. During use of the closure device, this introducer is in position in the percutaneous opening in the wall of the blood vessel. Consequently, neither the insertion assembly nor the haemostatic material has access to the blood vessel through the incision channel; which is in contrast to closure devices known in the state of the art. In FIG. 2 is illustrated how the attachment member 6 of the closure device 1 is attached to an introducer 7, the distal end of which has been inserted into a vessel through a puncture hole in the vessel wall. Herein the term "introducer" is intended to encompass all types of medical devices having a distal portion that extends into a vessel and a proximal portion that extends out from a patient's skin (or other tissue). As should be apparent from the following description, such an introducer remains in position during the complete operation of the insertion assembly.

Figure 3:
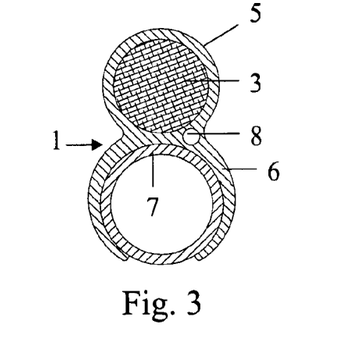
FIG. 3 shows the cross-section of the closure device and introducer of FIG. 2.

FIG. 3 shows the cross-section of the closure device 1 and the introducer 7 according to FIG. 2. In this embodiment, the closure device 1 is slidably connected to the introducer 7 by means of the attachment member 6, which is provided outside the distal portion of the retractable part 5. The attachment member 6 is generally tubular, with a slit extending along its length; thereby giving the distal portion of the closure device 1 a cross-section that has the general shape of the figure eight, with a portion being cut away at the base. From FIG. 2 and FIG. 3 it should be clear that the purpose of the slit is to make it possible to thread the attachment member 6 onto a tubular medical device, such as the introducer 7. By choosing a material with suitable flexibility (such as plastic) for the attachment member 6, it is possible to provide the closure device 1 with a dilatable attachment member 6, so that the closure device 1 can be attached to an introducer and then slid along the length of this introducer. The closure device 1 shown in FIG. 3 is further provided with a drip channel 8. The operations of the closure device 1 as well as the function of the drip channel 8 are going to be described in more detail below.

Referring again to FIG. 2, where the first step of a sealing operation is illustrated. Before this first step, a medical operation, such as a catheterization, on a patient has been completed, and an introducer 7, which was used during this medical operation, is still in position, i.e. the distal end of the introducer is inside a vessel, such as an artery, and the proximal end of introducer extends out of the patient's skin. In the first step of the sealing operation, the dilatable attachment member 6 is snapped onto the proximal end of the introducer 7. Thus, the insertion assembly 2 of the closure device 1 is now slidably connected to the introducer 7. In this state, the distal portion of the retractable part 5 extends from the distal portion of the stationary part 4, which leaves space enough to accommodate a charge of the haemostatic material 3 (indicated with dashed lines) in the distal portion of the insertion assembly 2.

Figure 4:
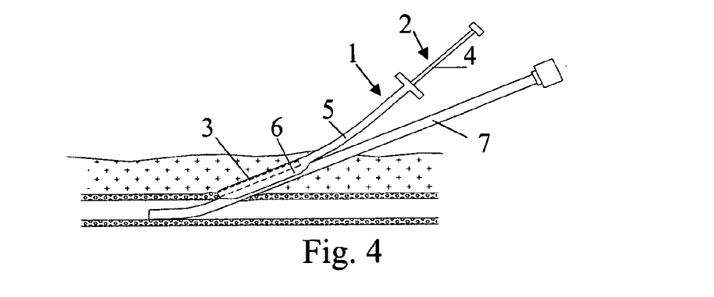
FIG. 4 illustrates the second step of the sealing operation.

FIG. 4 shows the completion of the second step in the sealing operation. In the second step, the insertion assembly 2, still being connected to the introducer 7 by means of the attachment member 6, is slid along the length of the introducer 7 until the distal end of the insertion assembly 2 is in contact with the outer surface of the vessel wall. When accomplishing this second step, a surgeon pushes the insertion assembly 2 through the incision channel, in which the introducer 7 is already positioned, thereby dilating the incision channel and compressing the surrounding tissue. If, for example, the sealing operation is performed at the femoral artery in the groin, the tissue surrounding the artery is mainly composed of adipose tissue, through which the insertion assembly 2 can be advanced relatively easily. Having in mind that vessel walls mainly are composed of fibrous tissue, which provides a significant resistance against further movement of the insertion assembly 2, the surgeon is provided with a readily detectable indication that the distal end of the insertion assembly 2 is in contact with the outer vessel wall. Furthermore, since the tissue in the edges of the dilated puncture hole in the vessel wall is in a stretched state, the risk that the insertion assembly 2 unintentionally is pushed through the puncture hole and into the vessel is minimal. In order to further reduce this risk, two more measures may be taken. These measures, which are to be described below, involve the drip channel mentioned above and an insertion assembly being provided with a distal tip that is bent upwards.

Figure 5:
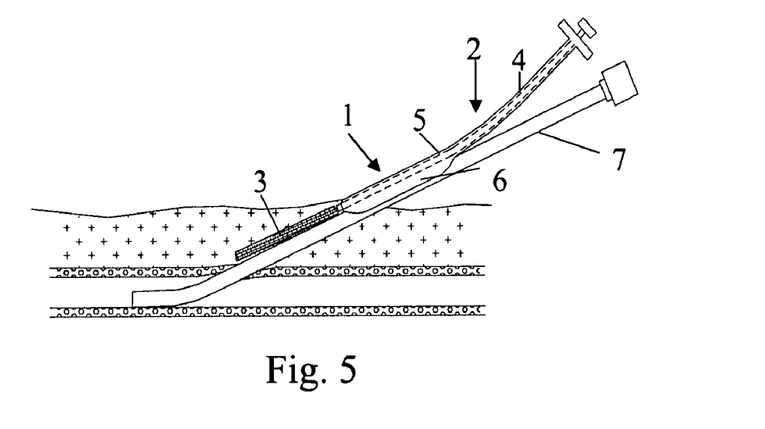
FIG. 5 illustrates the third step of the sealing operation.

In FIG. 5, the third step of the sealing operation has been completed. In the third step, the retractable part 5 is retracted over the stationary part 4 (indicated with dashed lines), thereby disengaging the haemostatic material 3 from the insertion assembly 2. Since the distal end of the stationary part 4 is in contact with the charge of haemostatic material 3, the haemostatic material 3 is prevented from being retracted by the retracting movement of the retractable part 5. When the third step of the sealing operation has been completed, the haemostatic material 3 is positioned in the incision channel leading to the puncture hole in the vessel wall. In this context it should be noted that the introducer 7 is still in position in the puncture hole in the vessel wall and there is no significant bleeding from the vessel.

Figure 6:
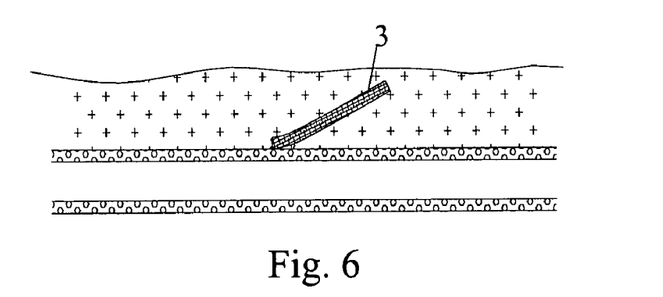
FIG. 6 illustrates the sealing member after the completion of the sealing operation.

FIG. 6 illustrates the completion of the fourth step in the sealing operation. In this final step, the closure device is slid backwards along the introducer and is then disconnected from the introducer and disposed of before the introducer is removed and disposed. As an alternative, the introducer may be retracted from the incision channel with the closure device still being connected. When the sealing operation has been completed, only the haemostatic material 3 is left in the incision channel, as is illustrated in FIG. 6. By providing the haemostatic material 3 with a suitable clotting agent, such as thrombin or chitosan, the time until complete haemostasis is achieved can be limited to a few minutes. If needed, applying an external pressure, either manually or by a suitable compression device, may assist the sealing operation.

Before finishing the discussion of the sealing operation, the special advantages with closure device according to the invention should be noted. During the above-described steps of the sealing operation, no parts of the closure device have had access to the vessel, and the positioning of the haemostatic material involves retracting movements only. Consequently, the risk that the haemostatic material of the closure device unintentionally is deployed inside the vessel is minimal; which is in contrast to closure devices known in the state of the art where a sealing member or a haemostatic material usually is positioned in the incision channel by means of a pushing movement in the forward direction, i.e. towards the opening in the vessel wall.

Figure 7:
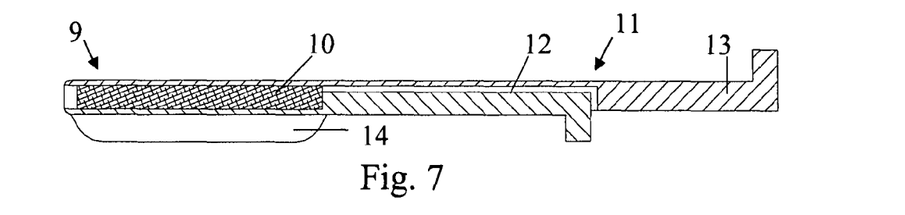
FIG. 7 shows schematically a second embodiment of a closure device in an initial state.

In the embodiment shown in FIG. 1, the retractable part 5 extends from the stationary part 4, or, with other words, the distal portion of the retractable part 5 constitutes the distal portion of the insertion assembly 2. Another embodiment of a closure device 9 is shown in FIG. 7. The closure device 9 comprises a haemostatic material 10 and an elongated insertion assembly 11, which comprises an elongated stationary part 12, an elongated retractable part 13 and an attachment member 14. The attachment member 14, which has the same shape as the attachment member 6 of the first embodiment, is attached to the outside of the stationary part 12. In this embodiment, the retractable part 13 has the general shape of a rod, which is provided with a recess that extends in the distal direction of the retractable part 13. The inner wall of the recess in the retractable part 13 is in slidable engagement with the proximal portion of the stationary part 12. The stationary part 12 has also the general shape of a rod, which is provided with a recess that extends in the distal direction of the stationary part 12. The recess in the stationary part 12 is shorter than the recess in the retractable part 13. In FIG. 7, the closure device 9 is depicted in an initial state, with the distal ends of the stationary part 12 and the retractable part 13 being in the same plane, i.e. the recess in the stationary part 12 and the recess in the retractable part 13 constitute together the distal portion of the insertion assembly 11 and provide the hollow space that contains the haemostatic material 10. The proximal end of the recess in the stationary part 12 is in contact with the haemostatic material 10, thereby preventing the haemostatic material 10 from being retracted by a retracting movement of the retractable part 13.

Whether or not the last feature, that the stationary part has a transverse portion, such as the end of a recess or the end of the stationary part, is essential for the closure device depends on the characteristics of the haemostatic material. For example, a haemostatic material in the form of a plug made from a solid material that easily slides inside the insertion assembly may require such a transverse portion, which prevents the plug from being retracted by the retracting movement of the retractable part. On the other hand, for a haemostatic material in the form of a sponge like material such a transverse portion may be redundant. Excluding a transverse portion may be advantageous in that different lengths of the charge of haemostatic material can be accommodated in the same insertion assembly.

Figure 8:
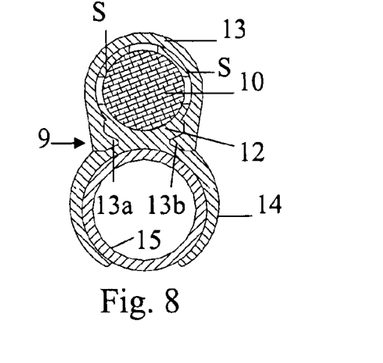
FIG. 8 shows the cross-section of the closure device of FIG. 7.
Figure 15:
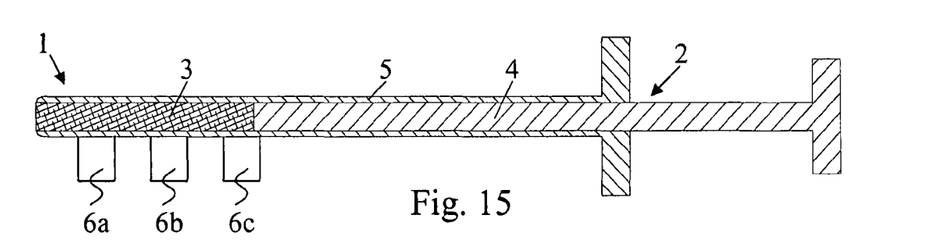
FIG. 15 shows a sixth embodiment of a closure device.

FIG. 8 shows the cross-section of the closure device 9, which is connected to an introducer 15 by means of the attachment member 14. The figure illustrates how the stationary part 12 and the retractable part 13 together provide the space in which the haemostatic material 10 is contained. FIG. 8 also shows spacers/guides S between retractable part 13 and haemostatic material 10. It can also be seen that the retractable part 13 is in slidable engagement with the stationary part 12 by means of projections 13a and 13b from the retractable part 13 that engage in grooves in the stationary part 12. Such projections and grooves may have a variety of different shapes. The attachment member 14 is attached to the distal portion of the stationary part 12, and a comparison of FIG. 8 with FIG. 3 reveals the difference between the attachment member 14 and the attachment member 6 of FIG. 3. Whereas the attachment member 6 is attached to the retractable part 5 of the closure device 1, the attachment member 14 is attached to the stationary part 12 of the closure device 9. This means that, during the retracting movement, the attachment member 14 remains in position on the introducer 15, which may facilitate a smooth operation of a closure device according to the present invention. Here it should be noted that instead of providing a single attachment member, a number of attachment members, e.g. in the form of flexible rings each provided with a slit (for example, rings 6a, 6b, and 6c shown in FIG. 15), could be arranged spaced apart along the length of an insertion assembly.

Figure 9:
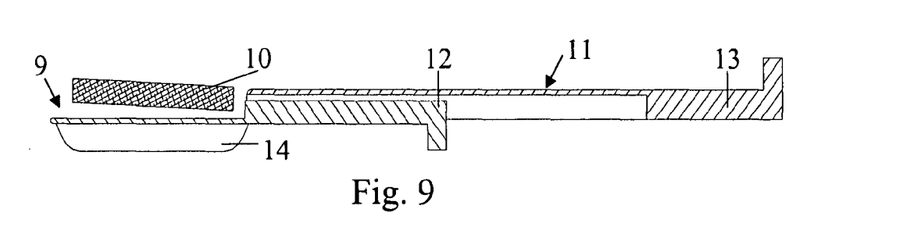
FIG. 9 shows the closure device of FIG. 7 in a disengaging state.

In FIG. 9, the closure device 9 is illustrated in a state that corresponds to the third step of the sealing operation described in connection with FIG. 5. In this third step, the retractable part 13 is retracted, which disengages the haemostatic material 10 from the insertion assembly 11. As can be seen from the figure, this retraction movement does not affect the attachment member 14, since it is connected to the stationary part 12. The introducer and the insertion assembly 11 are removed in a subsequent step.

Figure 10:
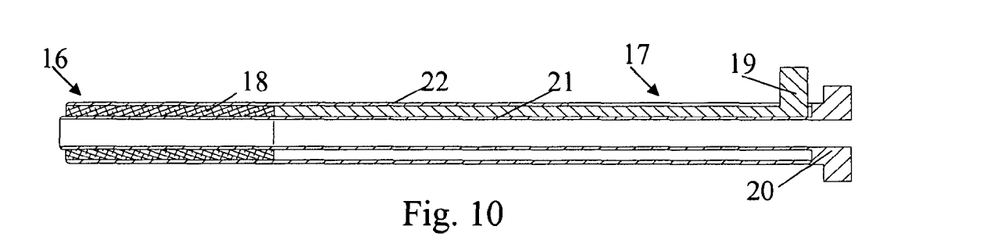
FIG. 10 shows schematically a third embodiment of a closure device.

In the embodiments shown in FIG. 1 and FIG. 7, respectively, the closure devices have been provided with an attachment means, such as attachment members 6 and 14, that virtually operates a separate part of the insertion assembly, i.e. the elongated insertion assembly slides as a separate part on the outside of the introducer. This is not to say that the attachment member actually is provided as a separate part to an existing insertion assembly, or that the attachment member has to be manufactured in a separate manufacturing step. In FIG. 10 is shown a third embodiment of a closure device 16. The closure device 16 comprises an elongated insertion assembly 17 and a charge of a haemostatic material 18. The insertion assembly 17, in turn, comprises an elongated stationary part 19 and an elongated retractable part 20. The retractable part 20 is in the form of a hollow sheath having an inner wall 21 and an outer wall 22. The charge of haemostatic material 18 is disposed between the inner wall 21 and the outer wall 22 in the distal portion of the retractable part 20. A slit 23 (not seen in the figure) extends along the length of the retractable part 20. The stationary part 19 has the general shape of a rod and is provided opposite to the slit 23 between the inner wall 21 and the outer wall 22, so that the retractable part 20 is in slidable engagement with the stationary part 19, and the distal end of the stationary part 19 is in contact with the proximal end of the charge of the haemostatic material 18. By means of this slit 23, which goes into the interior of the hollow retractable part 20, the insertion assembly 17 is slidably connected to an introducer, as is more easily recognized from FIG. 11.

FIG. 11 shows the cross-section of the closure device 16 connected to an introducer 22a. In particular, the slit 23 is visible. By means of this slit 23 and by manufacturing the retractable part 20 from a flexible material (such as plastic), the retractable part 20 can be snapped onto an introducer, such as introducer 22a. Consequently, the slit 23 constitutes the attachment means for this embodiment of a closure device and replaces fastening means attached to the exterior of an insertion assembly. In this third embodiment, the slit 23 is only a narrow gap between the longitudinal edges of the hollow sheath that basically constitutes the retractable part 20. Further, the inner wall 21 and the outer wall 22 extend essentially all the way from the first longitudinal edge to the opposing second longitudinal edge, i.e. as much space as possible has been obtained for the haemostatic material 18.

In FIG. 12 is shown the cross-section of a fourth embodiment of a closure device 24 connected to an introducer 25. The closure device 24 comprises a haemostatic material 26, which is contained in the distal portion of a retractable part 27. In this embodiment, the retractable part 27 has basically the form of a hollow sheath, with a rather large portion being cut away along its length. This cut-away portion (indicated with reference numeral 28) replaces the more narrow slit 23 described above in connection with FIG. 10 and FIG. 11. The wall of the hollow sheath that basically constitutes the retractable part 27 becomes thinner towards its longitudinal edges, thereby making it easy to thread the insertion assembly onto an introducer. Further, a cavity, which extends along the length of the retractable part 27, is provided opposite to the cut-away portion 28, where the wall of the retractable part 27 has its largest thickness. This cavity, in which the haemostatic material 26 is contained, occupies only a part of the circumference, i.e. the cavity does not extend all the way from the first longitudinal edge to the opposing second longitudinal edge.

Figure 13:
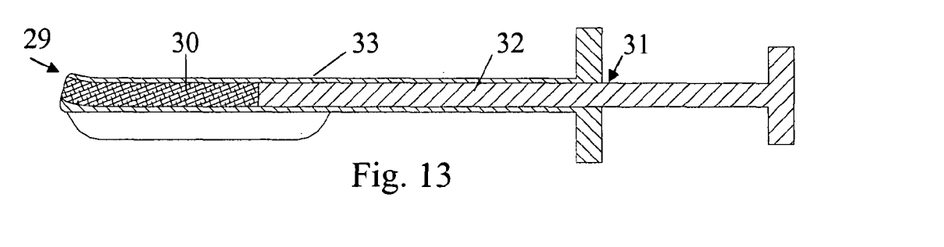
FIG. 13 shows schematically a fifth embodiment of a closure device.

As was mentioned above, two precautionary measures may be taken in order to further reduce the risk that an insertion assembly unintentionally is pushed through a vessel wall. The first of these measures is illustrated in FIG. 13, where a fifth embodiment of a closure device 29 is shown. The closure device 29 comprises a haemostatic material 30 and an insertion assembly 31, which, in turn, comprises a stationary part 32 and a retractable part 33. The insertion assembly 31 is similar to insertion assembly 2 shown in FIG. 1, except that the distal end of the insertion assembly 31 is slightly bent upwards. The purpose of this configuration is that the upwardly bent tip further reduces the risk that the insertion assembly 31 by accident is pushed through a vessel wall and into the vessel. It should be understood that all of the embodiments described above and illustrated in the figures could be provided with such an upwardly bent (or blunt) distal end, although an upwardly bent tip only has been explicitly shown for one embodiment of the invention.

Figure 14:
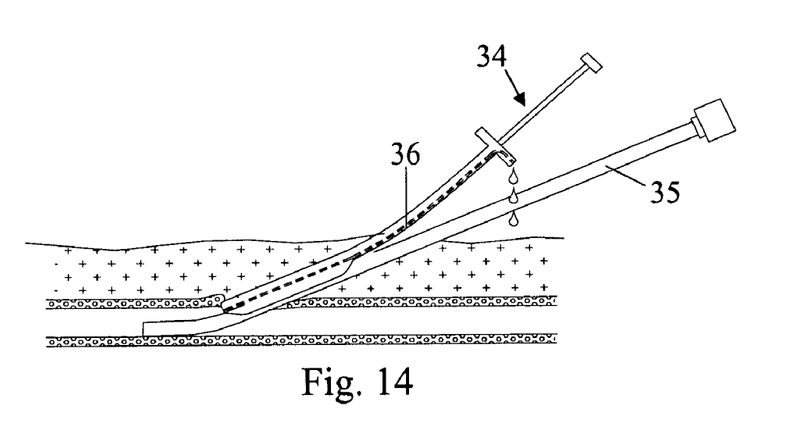
FIG. 14 illustrates a closure device that unintentionally has been introduced into a blood vessel and how this misplacement can be detected.

The second precautionary measure involves the drip channel 8 that was briefly mentioned in connection with FIG. 3. The function of such a drip channel is illustrated in FIG. 14, where an insertion assembly 34 has been attached to an introducer 35. The insertion assembly 34 is shown in a state where the insertion assembly 34 unintentionally has been pushed too far into the incision channel, so that the distal end of the insertion assembly has penetrated the vessel wall. The insertion assembly 34 is provided with a drip channel 36 (indicated with dashed lines) that extends from the distal end to the proximal end of the insertion assembly 34. As is illustrated in the figure, by means of the pressure that prevails inside the vessel, fluid is pressed into the inlet of the drip channel 36 and appears at the exit of the drip channel 36, thereby providing a user with a readily detectable indication that the insertion assembly 34 has penetrated the vessel wall. With other words, a requirement for a correctly positioned insertion assembly 34 is that there is essentially no fluid appearing from the proximal end of the drip channel 36. It should be understood that all of the embodiments described above and illustrated in the figures could be provided with a drip channel, although a drip channel only has been explicitly shown for one embodiment of the invention.

Although the present invention has been described with reference to specific embodiments, also shown in the appended drawings, it will be apparent for those skilled in the art that many variations and modifications can be done within the scope of the invention as described in the specification and defined with reference to the following claims.

What is claimed is:

1. A closure device assembly for sealing an incision channel extending from a tissue surface of a patient, through a wall of a vessel and into the vessel, in conjunction with an introducer whose proximal end is outside the tissue surface, said closure device assembly comprising:

the introducer, the introducer having an open distal end, a cylindrical outer surface, and a cylindrical inner surface defining a lumen configured for passing a medical instrument therethrough and through the open distal end of the introducer; and a closure device including:
- a body comprising a non-fluid haemostatic material; and
- at least one attachment mechanism, connected to the body, the attachment mechanism including:
  - a side opening dimensioned and configured such that the attachment mechanism is connectable to the introducer by approaching the introducer from a side, while longitudinal axes of the introducer and closure device are substantially parallel to each other, and applying force in at least a transverse direction to thereby snap the attachment mechanism on to a side of the introducer such that the body is off-set to a side of the introducer, and
  - a sliding surface configured such that the closure device is slidable along the cylindrical outer surface of the introducer,
- wherein the assembly is configured such that, when the closure device is initially attached to the introducer, both the haemostatic material and the attachment mechanism are located within at least a distal end portion of the body of the closure device.

2. A closure device assembly according to claim 1, wherein the body further comprises:
- a first part and a second part to contain the haemostatic material such that the haemostatic material is contained in the closure device while the first part and the second part are not moved relative to one another and such that the haemostatic material is delivered in the incision channel outside the vessel by moving the first part and the second part relative to one another.

3. A closure device assembly according to claim 2, wherein one of the first and second parts comprises projections and the other of the first and second parts comprises grooves,
- wherein the closure device is configured such that the first and second parts engage with one another by engaging the projections in the grooves.

4. A closure device assembly according to claim 3, wherein the one of the first and second parts further comprises spacers to create a space between the haemostatic material and the one of the first and second parts.

5. A closure device assembly according to claim 1, wherein the attachment mechanism comprises a tubular attachment member.

6. A closure device assembly according to claim 1, wherein the opening is in a form of a slit or a cut-away portion.

7. A closure device assembly according to claim 1, wherein the attachment mechanism is in a form of flexible rings, each of which is provided with a slit and which are arranged spaced apart.

8. A closure device assembly according to claim 1, wherein a distal end of the body is bent in a direction away from the longitudinal axis of the introducer.

9. A closure device assembly according to claim 1, wherein the haemostatic material comprises a solid.

10. A closure device assembly according to claim 1, wherein the haemostatic material is a solid.

11. A closure device assembly according to claim 1, wherein the haemostatic material is sponge-like.

12. A closure device assembly according to claim 1, further comprising a drip channel that extends from a distal end of the closure device towards a proximal end of the closure device.

13. A closure device assembly according to claim 1, wherein the body comprises a stationary part and a retractable part in slidable engagement with the stationary part,
- wherein the retractable part has a form of a hollow sheath having an inner wall and an outer wall, between which the haemostatic material is contained, and the stationary part, which has a shape of a rod, is provided between the inner wall and the outer wall.

14. A closure device assembly according to claim 13, wherein the attachment mechanism comprises a slit or cut-away portion in the inner and outer walls of the retractable part, such that the retractable part can be connected to the introducer so that at least a portion of the introducer is in contact with the inner wall of the retractable part.

15. A closure device assembly according to claim 14, wherein the attachment mechanism is formed as the slit or cut-away portion in the inner and outer walls of the retractable part,
- wherein the retractable part has an annular shape with adjacent ends separated by the slit, wherein the hollow sheath extends from one adjacent end to another adjacent end.

16. A closure device assembly according to claim 1, wherein the assembly is configured such that, when the closure device is initially attached to the introducer, both the haemostatic material located within the distal end portion of the body of the closure device and the attachment mechanism are located within a plane perpendicular to a long axis of the closure device.

* * * * *